United States Patent
Ziv et al.

(10) Patent No.: US 6,849,603 B1
(45) Date of Patent: Feb. 1, 2005

(54) PEPTIDES FOR INHIBITION OF APOPTOSIS AND PHARMACEUTICAL COMPOSITIONS CONTAINING THEM

(75) Inventors: Ilan Ziv, Kfar-Sava (IL); Anat Shirvan, Herzliya (IL)

(73) Assignee: NSS T Neurosurvival Technologies Ltd. (IL)

( * ) Notice: Subject to any disclaimer, the term of this patent is extended or adjusted under 35 U.S.C. 154(b) by 0 days.

(21) Appl. No.: 09/622,058

(22) PCT Filed: Feb. 16, 1999

(86) PCT No.: PCT/IL99/00096

§ 371 (c)(1),
(2), (4) Date: Dec. 29, 2000

(87) PCT Pub. No.: WO99/43701

PCT Pub. Date: Sep. 2, 1999

(30) Foreign Application Priority Data

Feb. 24, 1998 (IL) ................................. 123429

(51) Int. Cl.⁷ ........................... A61K 38/08; C07K 7/06
(52) U.S. Cl. ........................................ 514/15; 530/328
(58) Field of Search ............................ 514/15; 530/328

(56) References Cited

U.S. PATENT DOCUMENTS

| 5,910,442 A | 6/1999 | Gelman |
| 6,713,280 B1 * | 3/2004 | Huang et al. ............... 435/69.1 |

FOREIGN PATENT DOCUMENTS

| EP | 0 755 516 B1 | 12/1997 |
| IL | 125908 | 8/1998 |
| WO | WO 95/34315 | 12/1995 |
| WO | WO 96/29403 | 9/1996 |
| WO | WO 97/01760 | 1/1997 |
| WO | WO 97/35971 | 10/1997 |
| WO | WO 98/05777 * | 2/1998 |

OTHER PUBLICATIONS

S.M. Muchmore et al., "X–ray and NMR structure of human Bcl–$x_L$, an inhibitor of programmed cell death", Letters to Nature, vol. 381, May 23, 1996, pp. 335–341.

* cited by examiner

Primary Examiner—Robert A. Wax
(74) Attorney, Agent, or Firm—Nixon Peabody LLP; Jeffrey L. Costellia (57) ABSTRACT

The present invention relates to an isolated and purified peptide of the RY domain having an amino acid sequence of general formula (I) comprising a sequence of the following amino acids: $X_1—X_2—X_3—X_4—X_1—X_4—X_4—X_3—X_1$, $X_1$=Phe, Tyr, or any amino acid having a substituted aromatic residue; $X_2$=Glu, Asp, Ser, or any amino acid having a —$(CH_2)_n$—COO residue, wherein n=0–3; $X_3$=Asp, Thr, any aliphatic amino acid, or any of amino acids $X_4$; and $X_4$=Arg, Lys, or any amino acid having a —$(CH_2)_n$—$NH_3^+$ residue, or a —$(CH_2)_n$—NH—$C(NH_3^+)NH_2$ residue wherein n=0–4; as well as functional equivalents thereof. The invention relates also to pharmaceutical compositions comprising a compound of general formula (I), the use of said RY peptide and of said pharmaceutical composition in the preparation of a medicament and in method for the treatment of disorders of inappropriate activation of apoptosis; for increasing the number of viable cells in a biological tissue; and in a method for the enhancement for the survival of biological cells. The invention also relates to a method for the preparation of a RY-peptide of general formula (I). Furthermore, the invention also relates to an in vitro assay system for the regulation of cell death by the Bcl-2 family of test compounds (as hereinbefore defined).

14 Claims, 9 Drawing Sheets

Structure of the "RY domain" (F97-F105) within the Bcl-$x_L$ protein

PEPTIDES FOR INHIBITION OF APOPTOSIS AND PHARMACEUTICAL COMPOSITIONS CONTAINING THEM

CROSS REFERENCE TO RELATED APPLICATIONS

This application is a National Phase Application of PCT/IL99/00096, International Filing date Feb. 16, 1999, which claims the priority of Israeli Application IL 123429, filed Feb. 24, 1998.

BACKGROUND OF THE INVENTION

The present invention relates to the field of cell death, and more particularly, to apoptosis. The novel peptides and the compositions comprising said peptides are useful in inhibiting cell death. Therefore, they are potentially useful in treating disorders of inappropriate activation of cell death, such as neurodegenerative disorders, cerebral strokes, myocardial infarctions, etc.

Apoptosis is an intrinsic cell self-destruction or "suicide" program. In response to a triggering stimulus, cells undergo a highly characteristic cascade of events of cell shrinkage, blebbing of cell membranes, chromatin condensation and fragmentation, culminating in cell conversion to clusters of membrane-, bound particles (apoptotic bodies), which are thereafter engulfed by macrophages (Boobis A R, et al. Trends Pharmacol. Sci. 10:275–280, 1989; Bursch W, et al. Trends Pharmacol. Sci. 13:245–151, 1992.).

Normally, apoptosis plays important physiological roles, among others in the development of the central nervous system (Merry D E, et al. Development 10: 301–311, 1994.) However, it is now known that "inappropriate" activation of this death program also plays a critical part in the pathogenesis of numerous disorders, e.g. AIDS, ischemic injuries such as cerebral strokes or myocardial infarctions, and neurodegenerative disorders such as Alzheimer's disease, Parkinson's disease or amyotrophic lateral sclerosis (ALS) (Ziv I, et al. Neuosci Lett. 170: 136–140, 1994; Ziv I, et al. J. Neural. Transm. 49 (supp): 69–75, 1997; Thompson C B. Science 267:1456–1461.). The etiologies of the latter frequent and progressive neurological disorders are unknown. Thus, there are no known therapeutic measures capable of affecting the downhill course of the neuro-degenerative process. However, the substantiation of the role of apoptosis in the neuronal death in these disorders now delineates a novel window for therapeutic interventions, aimed to inhibit the final common biochemical pathway of the apoptotic process, upon which the various triggers of the death program converge.

The Bcl-2 family of proteins is a major system controlling this final common pathway. This growing family of proteins includes death-inhibitory members (Bcl-2, Bcl-xL, Bcl-w, Ced-9, Mcl-1, Al) as well as death inducers (Bax, Bak, Bcl-xS, Bad, Bik, Bid, Hrk) (Kroemer G. Nat. Med. 3:614–620, 1997; Reed J C. Nature 387:773–776, 1997.) This protein system has been shown to be a powerful regulator of cell death. Bcl-2 can protect cells from a wide array of insults, and can inhibit both apoptotic and necrotic modes of cell death (Shimizu S. Nature 374:811–813, 1995; Ziv I, et al. Apoptosis 2:149–155, 1997). On the other hand, transgenic Bcl-xL-knock-out mice manifest extensive apoptosis of neuronal tissues (Motoyama N, et al. Science 267:1506–1510), whereas neurons of Bax knock-out mice manifest resistance to apoptosis (Deckwerth T L, et al., Neuron 17:401–411, 1996). Clinical relevance of this protein system is reflected, among others, in reports of Bax upregulation following cerebral ischemia (McGibbon G A, et al. Brain Res. 750:223–234, 1997) and also in Alzheimer's disease brains and ALS spinal cord motor neurons (Su J H, et al. J. Neuropathol. Exp. Neuro. 56:86–93, 1997; Mu X, et al. Ann Neurol 40:379–386, 1996).

The members of the Bcl-2 family of proteins are strategically localized in the outer mitochondrial membrane, endoplasmic reticulum, nuclear envelope, and the cytosol (Kromer G. Nat Med 3:614–620, 1997; Reed J C Nature 387:773–776, 1997). Bcl-xL has a predominantly mitochondrial localization. Notably, Bcl-xL manifests high levels of expression in the central nervous system (Mizuguchi M, et al. Brain Res 712:281–286, 1996). Bax, a major death inducer, is predominantly cytosolic, but manifests redistribution to the mitochondria upon induction of apoptosis (Wolter K G, et al., J Cell Biol 139:1281–1292, 1997.

Amino acid sequence analysis of the Bcl-2 family yielded a focus on several regions within the proteins (Yin X M, et al. Nature 369:321–323, 1994; Sedlak T W, et al., Proc. Natl. Acad. Sci. USA, 92:7834–7838, 1995; Cheng E H, et al., Nature 379:554–556, 1996; Chittenden, T et al., EMBO J. 14:5589–5596, 1995; Hunter J. at al. J. Biol. Chem. 271:8521–8524, 1996; Wang K, et al., Genes Dev. 10:2859–1869, 1996). These regions are:

1. A hydrophobic C-terminal region, which serves for membrane anchoring.
2. BH1 and BH2: Regions which are important for formation of a hydrophobic binding cleft, where protein—protein interactions take place.
3. BH3: The C-terminal half of the amphipathic Bcl-xL second helix, serves as part of the hydrophobic binding cleft. The homologous region in the death-inducing family members, serves as a ligand region, and is important for their protein—protein interactions with other proteins within the family.
4. A flexible, cytosol-exposed PEST-like region in Bcl-2 and Bcl-xL, which serves as a regulator region. It includes serine phosphorylation sites.
5. BH4: an N-terminal region, which serves to stabilize the three dimensional protein structure, as well as a critical docking region for several proteins, e.g., Raf-1, Bag-1 and Ced-4.

The mode of action of the Bcl-2 family proteins in the regulation of cell survival is largely unknown, though two major; functions have been revealed:

1. Adaptor/Docking proteins: Bcl-2 and B1-xL, by virtue of their membrane attachment with cystolic orientation, have been shown to act as important adaptor or docking proteins, pulling-out proteins from the cytosol, thus inactivating them or orienting them to interact with other membrane-bound proteins. Among these are the protein kinase Raf-1, calci-neurin, R-Ras, H-Ras, the prion protein Pr-1, Bag-1, the p53-binding protein p53-BP2 and others (Kroemer G. Nat Med 3:614–620, 1997; Reed J C. Nature 387:773–776, 1997). Another important protein shown to be docked to Bcl-2 is the Apaf-1 protein. This death-inducing protein, homologous to the nematode *Caenorhabditis*-elegans protein CED-4, acts in mediating linkage between the Bcl-2 system and the downstream cysteine proteases (caspases), which perform the execution phase of the death program. (Zou H et al., Cell 90:405–413, 1997; Yuan J., et al., Development 116:309–320, 1992; Chinnaiyan A M, et al., Science 275:1122–1126, 1997)
2. Formation of transmembrane pores and/or ionic channels, as suggested by the similarity of the crystal structure of Bcl-xL and the structure of pore forming bacterial toxins, e.g. colicins and diphtheria toxin (Muchmore, et al., Nature 381:335–344;1996). Bcl-xL, Bcl-2 and Bax have all been shown to be capable of transmembrane ionic channel formation, the two formers only in acidic pH, whereas the latter also in physiological pH. (Minn A J, et al. Nature 385:353–357, 1997; Schendel S L, et al. Proc. Natl. Acad. Sci. USA 94:5113–5118, 1997; Antonsson B et al., Science 277:370–372, 1997; Schlesinger P H, et al., Proc. Natl. Acad. Sci. USA 94:11357–11362, 1997).

These structure-function considerations and the localization of the Bcl-2 and Bcl-xL to the outer mitochondrial membrane, are in accordance with the emerging importance of the mitochondrial level in the apoptotic cascade (Zamzami N, et al. J. Exp Med 183:1533–1544, 1996). Disruption of the mitochondrial transmembrane potential has been shown to be an early event in apoptosis (Zamzami N, et al., J. Exp Med 181:1661–1672, 1995). Evidently, this derangement involves the opening of so-called mitochondrial permeability transition pores (PTP) (Zamzami N, et al., J Exp Med 182:367–377,1995). These are megachannels, which can be opened in response to numerous noxious stimuli and lead to redistribution of molecules of <1,500 daltons, thus disrupting mitochondrial membrane potential and associated mitochondrial functions (Zoratti M, et al., Biochim Biophys Acta 1241:139–176, 1995). Chemical inducers and inhibitors of the PTP have been shown to induce or inhibit apoptosis, respectively (Marchetti P, et al., Apoptosis 1:119–215, 1996; Zamzami N, et al., FEBS Letters 384:53–57, 1996). Moreover, during the apoptotic process, mitochondria have been shown to liberate at least three mediators of apoptosis: ceramide, cyctochrome c, and AIF; (apoptosis-inducing factor) a 50 kDa protein with caspase-like activity (Marchetti P, et al., Apoptosis 1:119–125, 1996). Interestingly, all these mitochondrial-dependent steps in the apoptotic process have been effectively blocked by Bcl-2 (Zamzami N, et al., J Exp Med 182:367–377, 1995; Kluck R M, et al., Science 275:1132–1136, 1997; Susin S, et al., J Exp Med 184:1331–1342, 1996).

Specific importance is currently attached to the release from the mitochondria of cytochrome C, which acts to activate the downstream apoptotic cascade, and can be liberated and exert its pro-apoptotic activity even in the absence of mitochondrial potential collapse (Bossy-Wetzel E, et al. EMBO J, 17:37–49, 1998; Li F, et al J Biol Chem, 272:30299–30305,1997).

The Bcl-2 system is therefore a powerful system in determining cell fate. For purposes of the development of novel diagnostics and therapeutics for modulation of cell death, it has therefore been desirable to identify specific regions or domains within these proteins which are, by themselves, capable of fulfilling at least part of the functions of the whole proteins. For example, the identification of agents capable of mimicking the apoptosis-inhibitory effects of Bcl-2 and Bcl-xL may be useful for the treatment of medical disorders associated with inappropriate activation of the death program, for example, neurodegenerative disorders, ischemic injury (cerebral stroke, myocardial infarction), AIDS, myelodysplastic syndromes, traumatic or toxic injuries.

DETAILED EMBODIMENTS OF THE INVENTIONS

The present invention relates to a novel protein domain which is useful in inhibiting cell death, and which has been identified and mapped to a short domain of 9 amino acids which is called hereinafter "RY domain" and which is mapped on the central portion of the relevant protein.

Said RY domain is:

1. Significantly conserved through evolution: Comparison of the Bcl-xL amino acid sequence from chicken, mouse, rat and human, revealed conservation of this motif between species. Conservation through evolution is usually considered to mark structural/functional importance.

2. Similar among death inhibitors: Comparison of the "RY domain" of the death inhibitors: Bcl-2, Bcl-xl and Bcl-w revealed marked similarity:

Bcl-xL: Phe-Glu-Leu-Arg-Tyr-Arg-Arg-Ala-Phe (FELRYRRAF) (SEQ ID NO:1)

Bcl-2: Phe-Ser-Arg-Arg-Tyr-Arg-Arg-Asp-Phe (FSRRYRRDF) (SEQ ID NO:2)

Bcl-w: Phe-Glu-Thr-Arg-Phe-Arg-Arg-Thr-Phe (FETRFRRTF) (SEQ ID NO:3)

Figure 1:
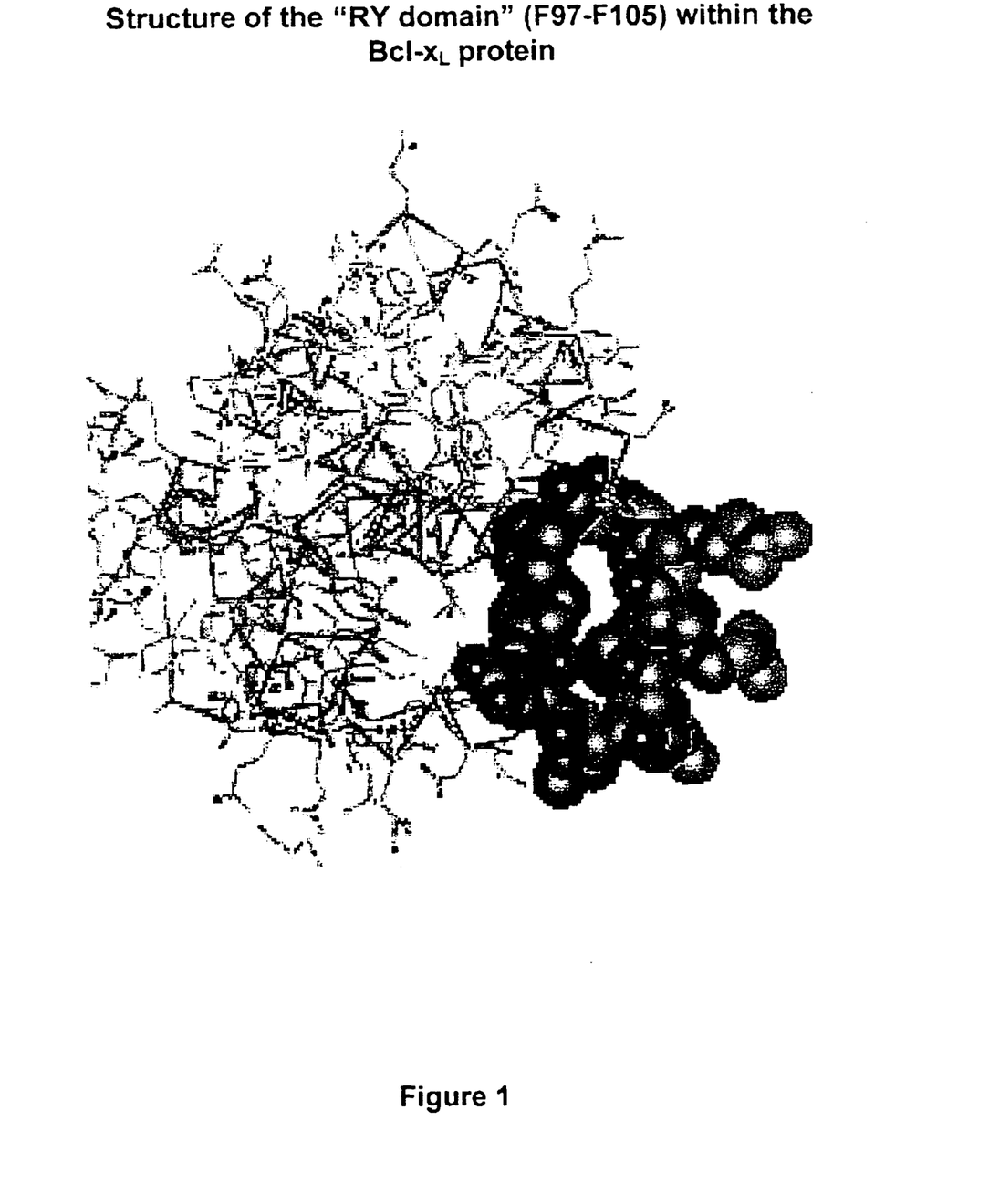
FIG. 1: Structure of the RY region

3. Located on the outer surface of the protein, as observed in the NMR and x-ray protein solution and crystal structures of Bcl-xL (Muchmore S W, et al., Nature 381:335–341, 1996; Brookhaven Protein Data Bank, Accession No. 1LXL and 1MAZ, respectively). These structural data also reveal that this small region forms an almost closed loop within the protein structure, with the Phe1 and Phe9 in close spatial proximity, while the Arg side-chains face the outside of the protein (FIG. 1).

4. Undergoing conformational change upon binding of Bcl-xL to a peptide from the BH3 region of a death inducer (Bak):

A systematic comparison has been performed of the structure of the free Bcl-xL (Muchmore S W, et al., Nature 381:335–341, 1996) and its structure upon binding to the BH3 peptide of Bak (Sattler M, et al., Science 275:983–986, 1997). In its unbound conformation, the second helix of the protein encompasses 15 amino acids (Ala84-Glu98). The RY domain in this conformation is the loop described above (FIG. 1.) However, upon binding of the BH3 peptide of Bak to the hydrophobic cleft of Bcl-xL, the RY domain undergoes a conformational change and becomes a part of the second helix, which now extends to residue Arg103 (Sattler M, et al., Science 275:983–986, 1997). Moreover, upon binding, several of the RY residues become engaged in interactions with the death-inducer peptide (i.e., Phe97, Arg100, Tyr101, Phe105).

5. Markedly different in cell death inhibitors vs. inducers: Death inhibitors:

Bcl-xL: FELRYRRAF (Phe-Glu-Leu-Arg-Tyr-Arg-Arg-Ala-Phe)(SEQ ID NO:1)

Bcl-2: FSRRYRRDF (Phe-Ser-Arg-Arg-Tyr-Arg-Arg-Asp-Phe)(SEQ ID NO:2)

Bcl-w: FETRFRRTF (Phe-Glu-Thr-Arg-Phe-Arg-Arg-Thr-Phe)(SEQ ID NO:3)

Death inducers:

Bax: LDSNMEL (Leu-Asp-Ser-Asn-Met-Glu-Leu)(SEQ ID NO:4)

Bak: INRRYDSEF (Ile-Asn-Arg-Arg-Tyr-Asp-Ser-Glu-Phe)(SEQ ID NO:5)

It has been found that the peptide FELRYRRAF is a potent inhibitor of cell death.

The present invention thus consists in an isolated and purified peptide of the RY domain, having an amino acid sequence of general formula I:

$X_1$=Phe, Tyr, or any amino acid having a substituted aromatic residue;

$X_2$=Glu, Asp, Ser, or any amino acid having a —$(CH_2)_n$—$COO^-$ residue, wherein n=0–3;

$X_3$=Asp, Thr, any aliphatic amino acid, or any of amino acids $X_4$; and $X_4$=Arg, Lys, or any amino acid having a —$(CH_2)_n$—$NH_3^-$ residue, or a —$(CH_2)_n$—NH—$C(NH_3^+)NH_2$ residue wherein n=0–4;

as well as functional equivalents thereof.

By "functional equivalents" is meant a compound possessing a biological activity or/and immunological characteristic similar to that of the RY domain of general formula I. Said term includes fragments, variants analogs, homologs and chemical derivatives possessing such activity or characteristic.

Specific peptides having the sequence of general formula I are hereinafter called Death Inhibitory Peptides or DIP.

Any of the above amino acids may be either the D- or the L-isomer.

The amino acid residues may also be residues of suitable synthetic amino acids.

Methionine (Met) may be connected to the N-terminal of the sequence of general formula I and this sequence is also within the scope of the present invention.

In an advantageous sequence of general formula I the sequence $X_4$—$X_1$—$X_4$—$X_4$ stands for Arg-Tyr-Arg-Arg;

In a further embodiment said sequence is preceded by $X_3$=Arg.

The substituted aromatic residue of $X_1$ is preferably Phenyl-$(CH_2)_n$—, wherein n 0–3.

The aliphatic amino acid of $X_3$ is preferably selected among Leu, Ile, Ala, Gly and Val.

The preferred sequence according to the present invention is DIP1, having the following amino acid sequance: Phe-Glu-Leu-Arg-Tyr-Arg-Arg-Ala-Phe (FELRYRRAF)(SEQ ID NO:1)

Said sequence corresponds to residues 97–105 of the Bcl-xL protein.

Additional sequences which may be considered as suitable death inhibitors are:

DIP2, having the following amino acid sequance: Phe-Ser-Arg-Arg-Tyr-Arg-Arg-Asp-Phe (FSRRYRRDF) (SEQ ID NO:2)

Said sequence corresponds to residues 104–112 of the Bcl-2 protein.

DIP3, having the following amino acid sequance: Phe-Glu-Thr-Arg-Phe-Arg-Arg-Thr-Phe (FETRFRRTF) (SEQ ID NO:3)

Said sequence corresponds to residues 53–61 of the Bcl-w protein.

The present invention consists also in pharmaceutical compositions comprising as active ingredient of the DIP, as defined above.

In a preferred embodiment the pharmaceutical composition comprises in addition to the DIP a pharmaceutically acceptable carrier.

The pharmaceutical compositions may be, e.g. tablets, id capsules, solutions, emulsions, etc. The carriers may be selected among any suitable components, e.g. solvents; emulgators; excipients; talc; flavors; colors; etc. The pharmaceutical composition may comprise, if desired, also other pharmaceutically active compounds.

The amount of the DIP incorporated in the pharmaceutical composition may vary widely. The factors which have to be considered when determining the precise amount are known to those skilled in the art. Such factors include, inter alia, the pharmaceutical carrier being part of the composition, the route of administration being employed and the frequency with which the composition is to be administered.

The pharmaceutical composition may be administered by any of the known methods, inter alia, per os, intravenous, intrapertioneal, intramuscular or subcutaneous or topical administration.

The present invention further consists in the use of a DIP or of a pharmaceutical composition as defined above in the preparation of a medicament, in particular for the modulation of cell death.

The present invention also consists in a method for the treatment of disorders of inappropriate activation of apoptosis by a DIP or by a pharmaceutical composition as defined above.

The present invention also consists in a method for increasing the number of viable cells in a biological tissue by a DIP or by a pharmaceutical composition as defined above.

The present invention also consists in a method for enhancement of the survival of biological cells by a DIP or by a pharmaceutical composition as defined above.

Moreover, the present invention further consists in a method for the preparation of a DIP of general formula I which comprises attaching the corresponding amino acids, one after the other, onto a functionalized resin, by the following steps:

a. sythesizing the sequence of Fmoc (9-fluorenyl methoxycarbonyl)-$N^{alpha}$-protected amino acids activated in situ in a suitable synthesizer and coupling same to a preloaded resin, removing the protecting group and repeating the coupling and deprotecting steps until the entire peptide synthesis has been finalized;

b. cleaving the peptide from the resin; and c. purifying the peptide obtained in step b.

The synthesizing step is preferably performed by using an ABI (Applied Biosystems U.K.) 433A synthesizer.

The coupling reagent is preferably HBTU/HOBt (benzotriazole-N,N,N',N'-tetramethyl-uronium hexafuorophosphate/N-hydroxybenzotriazole).

Preferably 3 equivalents of each of the activated amino acid is used in each coupling step The activation is preferably performed by HBTU/HOBt.

The resin used is a Wang resin or a 2-chlorotrityl resin.

The cleaving operation is preferably performed by acidolysis.

The peptide obtained in step b. is advantageously purified by RP-HPLC (Reversed Phase-High Performance Liquid Chromatography).

The peptide obtained in step c. is advantageously characterized using HPLC, nuclear magnetic resonance (NMR) and/or fast atomic bombardment-mass spectra (FAB-MS).

The sequence of amino acids as defined in general formula 1 may be connected to methionine by methods known per se such as chemical or biological molecular methods.

There has also been developed an in vitro assay system for the evaluation of the regulation of cell death by the Bcl-2 family of proteins. For this purpose:

A cellular assay system for the activity of the major members of the Bcl-2 family, e.g. Bcl-2 and Bax, and their interactive effects has been constructed in cultured cell lines. (This assay may be used for any member of the Bcl-2 family and for checking the combined effect of each 2 members of this family.) This simple and rapid assay system may be useful in testing the effect of various compounds in modulation of this powerful regulator of cell survival.

This assay is based on transient transfection of cultured cells (e.g., HeLa cells, SH-SY5Y neuroblastoma cells. PC12, pheochromocytoma cells, 293 kidney cells, primary neuronal cells etc.), via electroporation or cationic-lipid-mediated transfection, by an expression vector, harboring a reporter gene (e.g. the gene encoding for beta-galactosidase, or the gene encoding for luciferase). Based on the consideration that gene expression requires high level of function and integrity of cellular systems, a direct correlation can be drawn between the activity of the protein encoded by the reporter gene, and the survival rates of the transfected cells. The reporter gene is co-transfected with a second expression vector, carrying either the bcl-2 or bax genes, therefore affecting the cellular apoptotic threshold towards life or death, respectively. In addition, transfection of cells with a combination of both bcl-2 and bax genes is performed, to examine the activity of each of these two proteins in opposing the death-inhibitory or promoting-effect of the other, respectively.

For the detection of the effects of compounds (hereinafter called "test compounds") as potential modulators of the activity of the Bcl-2 system, each test compound is tested by one of two modes of administration into the cells:

A. Small, membrane permeable test compound particles are administrated by addition to the extracellular medium; and B. Cell membrane-impermeable small test compound particles are administered by electroporation or by liposome-mediated transfection.

Sould the test compound be a peptide it may be tested by the following mode of administration into the cells:

Small peptides are constructed into expression vectors that contain DNA sequences, encoding for the desired peptide; said peptide is transfected into the cells via electroporation or cationic-lipid-mediated transfection.

Potential inhibitors of cell death are evaluated in this system by measuring their ability to overcome bax-induced death process.

Potential triggers of apoptosis are assessed in this system by measuring their ability to induce cell death by themselves, their activity in counteracting Bcl-2 activity, and/or their effect in augmenting Bax cellular toxicity.

The present invention thus also consists in an in vitro assay system for the regulation of cell death by the Bcl-2 family of test compounds (as herein defined), which comprises:

a. transient transfection of cultured cells via electroporation or cationic-lipid mediated transfection by an expression vector, harboring a reporter gene;

b. co-transfecting the reporter gene with a second expression vector, carrying either the death inhibitor or the death inducer genes, thus affecting the cellular apoptotic threshold towards life or death, respectively;

c. performing transfection of cells with a combination of both the death inhibitor and the death inducer genes to examine the activity of each of these two proteins in opposing the death-inhibitory or promoting-effect of the other, respectively;

d. testing the effects of the test compounds as potential modulators of the activity of the Bcl-2 system, by testing each test compound by one of the following two modes of administration into the cells:

e. 1. small, membrane permeable test compound particles are administered by addition to the extracellular medium;

2. cell membrane-impermeable small test compound particles are administered by electroporation or by liposome-mediated transfection;

f. evaluating the potential of the test compounds to inhibit cell death by measuring their ability to overcome bax-induced death process; and g. assessing the potential of the test compounds to trigger apoptosis by measuring their ability to induce death by themselves, their activity in counteracting Bcl-2 activity, and/or their effect in augmenting Bax cellular toxicity.

Sould the test compound be a peptide it may be tested by the following mode of administration into the cells:

Small peptides are constructed into expression vectors which contain DNA sequences, encoding for the desired peptide; said peptide being transfected into cells via electroporation or cationic-lipid-mediated transfection;

Said in vitro assay will be exemplified in detail for a test compound being a peptide hereinafter in example 3.b.3.

The present invention will now be illustrated with reference to the following Examples and the accompanying Figs. without being limited by same. (The DIP illustrated in the Examples and Figs. is DIP1 Phe-Glu-Leu-Arg-Tyr-Arg-Arg-Ala-Phe {FELRYRRAF}.)

EXAMPLES

Example 1

Synthesis of a DIP

Peptide synthesis was performed using ABI 433A peptide synthesizer with HBTU/HOBt (benzotriazole-N,N,N',N'-tetramethyl-uronium hexafuorophosphate/N-hydroxybenzotriazole) coupling reagents. Amino acids used were Fmoc (9-fluorenyl methoxycarbonyl)-N$^{alpha}$-protected. Trifunctional amino acids were side-chain protected as follows: Arg [Pmc (2,2,5,7,8-pentamethyl chroman-6-sulphonyl)], Tyr [tBu (tertbutyl)], Glu [OtBu (terbutyl-ester)]. 330 µmol of preloaded Wang resin were placed in the reaction vessel. Each Fmoc amino acid was activated in situ using HOBt/HBTU, and subsequently coupled to the resin for 50 min. DIEA (Diisopropylethylamine) was used during coupling as a non nucleophilic base. The Fmoc protecting group on the alpha-amine was then removed with 20% piperidine in NMP (N-methylpyrrolidone) for 20 min. Three equivalents of the activated amino acids were employed in the coupling reactions. The deprotection and coupling steps were repeated with the addition of each subsequent amino acid until the peptide synthesis was completed. The final amino acid was deprotected using 20% piperidine in NMP, the peptide-resin was washed with NMP, followed by DCM (Dichloromethane), and dried in vacuum.

Cleavage from the Solid Support

A cleavage mixture consisting of TFA (Trifluoroacetic acid) 97.5% and TIS (Triisopropylsilane) 2.5% was added to the peptide-resin obtained in the previous step (20 ml cleavage mixture to 1 gr resin). The solution was stirred at room temperature for 60 min. The resultant slurry (resin) was filtered using a sintered glass filter. The resin was washed twice with TFA. The filtrate was concentrated to a volume of 1 ml using stream of nitrogen. Following the addition of cold diethyl ether (20 ml) the solution was cooled in an ice bath. After 60 min. the peptide was precipitated by centrifugation, washed with cold ether and dried in vacuum.

Purification and Characterization

The peptide obtained in the previous step was purified by RP-HPLC (reversed phase high performance liquid chromatography) on $C_{18}$ 5 μm Phenomenex Kromasil column (10 mm I.D.×25 cm). Samples were eluted using the following gradient:
(A): distilled $H_2O$, 0.05% TFA; (B) acetonitrile 0.05% TFA; (λ=214 NM; Flow 5 ml/min. The extent of purity for each peptide was monitored by rechromatography on $C_{18}$ 5 μm Phenomenex Kromasil column (4.6 mm I.D.×25 cm) analytical column, flow 1 ml/min. Characterization of the peptides was performed by FAB-MS (Fast atomic bombardment-Mass spectra).

The Peptide H-Phe-Glu-Leu-Arg-Tyr-Arg-Arg-Ala-Phe-OH: (SEQ ID NO:1)

Figure 2:
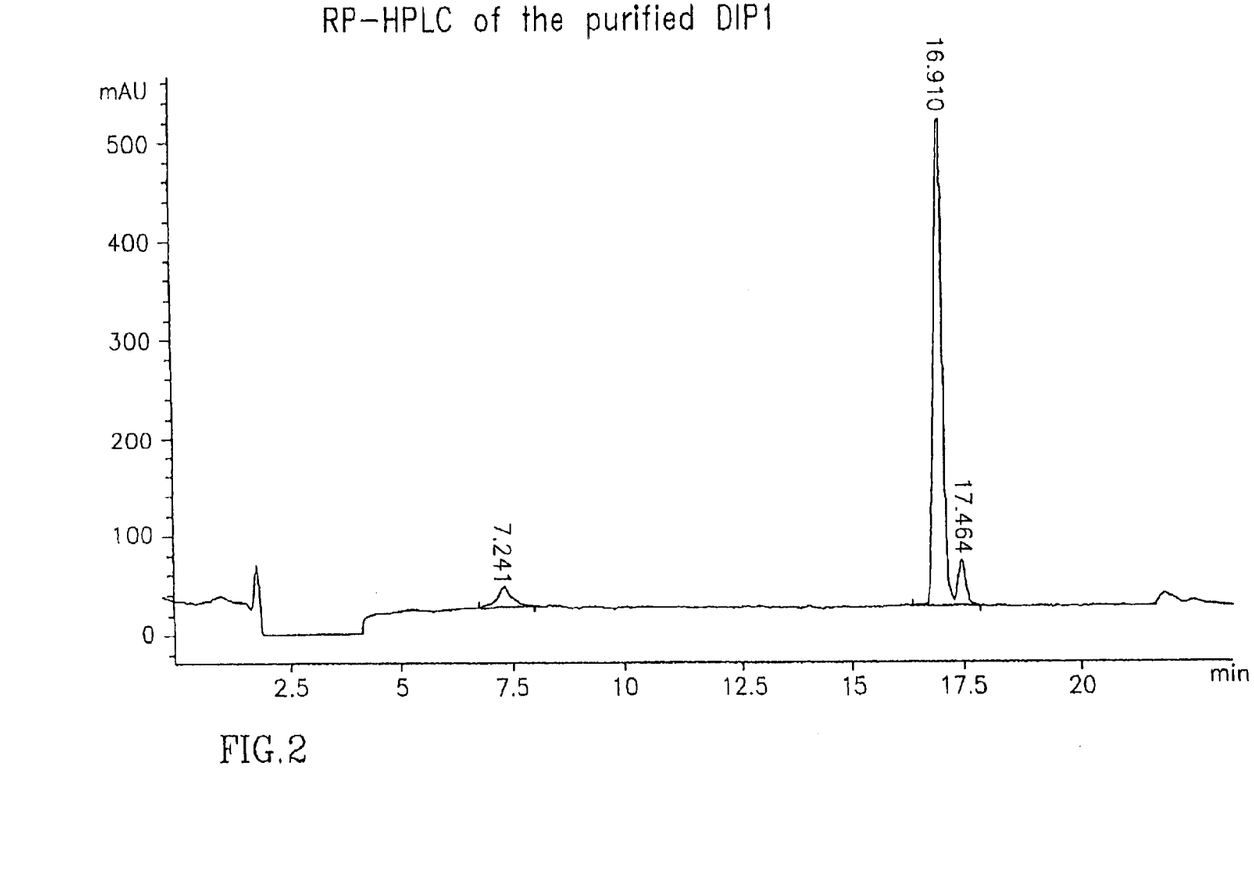
FIG. 2: RP-HPCL of the purified RY peptide
Figure 3:
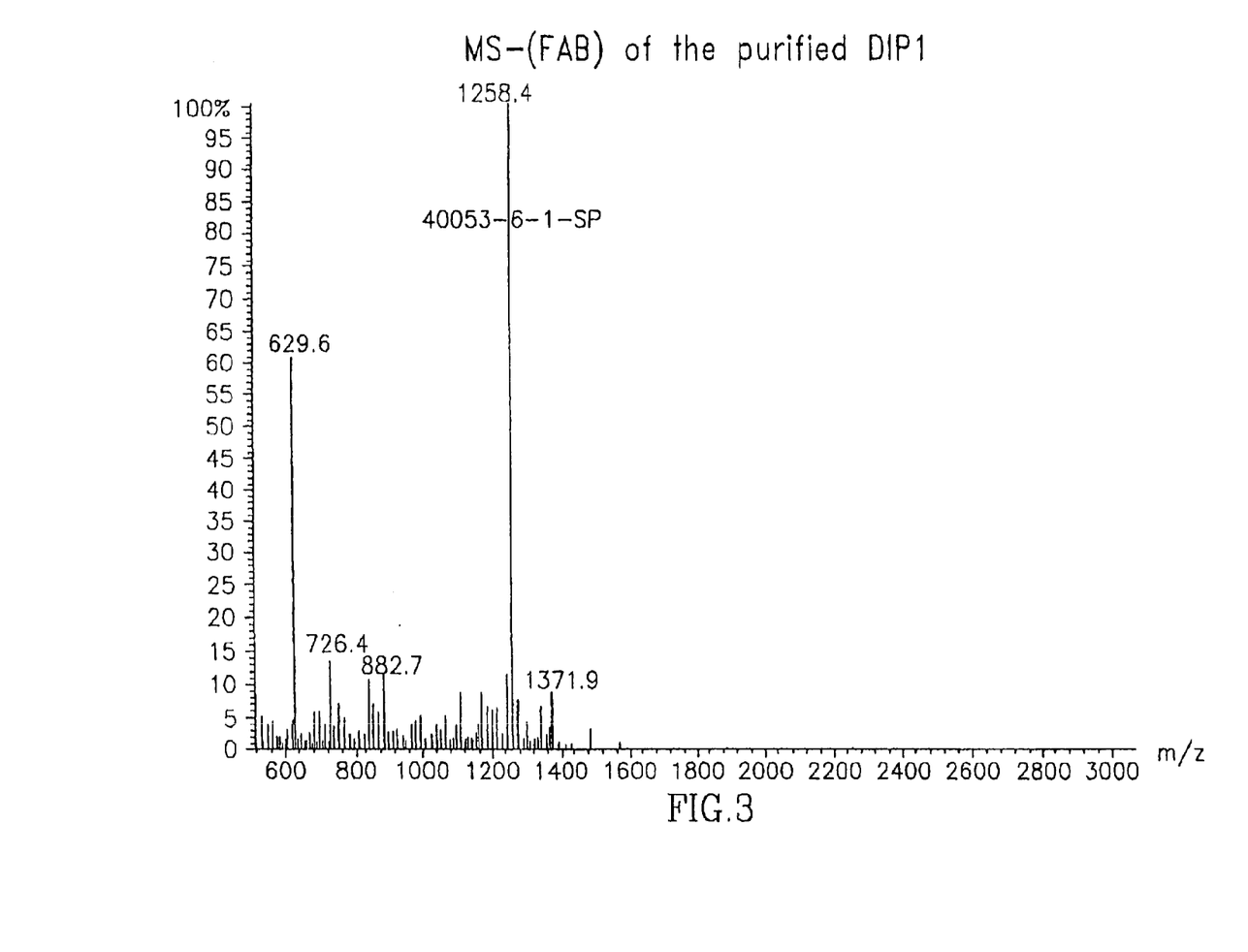
FIG. 3: MS-(FAB) of the purified RY peptide

After purification, the peptide obtained in the previous step was of 86.1% purity, as shown in FIG. 2 (non calibrated RP-HPLC, acetonitrile/water 0.1% TFA gradient from 5% to 50% acetonitrile at 30 min). FAB-MS calcd. m/Z for $C_{59}H_{89}N_{18}O_{13}$ (MH$^+$) 1257.7, found 1258.4 (FIG. 3).

Example 2

Construction of Expression Plasmid Encoding DIP1

Construction of DIP1-coding vector was done by means of polymerase chain reaction (PCR), and consisted of two steps:

1. Construction in pIRES-EGFP Expression Vector.

The nucleotide sequence encoding the 9 amino acids of the DIP peptide was included in a larger oligonucleotide, with both ends matching the sequences of the multi-cloning site of the expression vector pIRES-EGFP (Clontech). The sequence of this oligonucleotide was: 5'-CGACGGAATTC AGTGGATCCATGTTTGAACTGCGGTACCGGCGCGC GTTCTAGACTAGTAACGGCCGCCTG (SEQ ID NO:7)

In this oligonucleotide, the bold and underlined letters designate nucleotides encoding for the DIP, and the nucleotides before and after, are homologues to nucleotides 930–949 and 950–969 of the expression vector, respectively. In addition, this is oligonucleotide included recognition sites for the restriction enzymes EcoRI (external to the peptide-coding sequence) and PauI (in the peptide coding sequence). In addition, this oligonucleotide also included sequences coding for the amino acid Methionine, immediately preceding the sequence of the DIP peptide, to serve as a starting site for protein translation, and a translation stop codon, immediately following the sequence of the DIP peptide.

A second oligonucleotide contained sequences homologous to bases 1275–1250 of the expression vector. The sequence of this oligonucleotide was: 5'-GCGTCTAGATGC TCGACCTGCAGTTGGACCTGGG (SEQ ID NO:8). In this oligonucleotide, the recognition site for the restriction enzyme PstI was introduced, before (5' to) the vector homologous sequences. Both oligonucleotides were used in a PCR reaction, using the vector pIRES-EGFP as a template. PCR reactions were carried out as described by Ho S N et al. (Gene 77:51–59, 1989).

Following the PCR reaction, the reaction product was purified by gel electorphoresis in agarose, followed by purification with a Qiaquick PCR purification kit (Qiagene). The fragment obtained was then digested with the restriction enzymes EcoRI and PstI, and ligated into the vector pIRES-EGFP, digested with the same enzymes. The identity of the DIP peptide coding vector was confirmed by DNA sequence analysis.

2. Construction in the pcDNA3.1 Expression Vector:

The DNA fragment encoding for the DIP peptide was then subcloned into the expression vector pcDNA3.1, following its rescue from pIRES-EGFP by digestion with EcoRI and MscI restriction enzymes. The fragment was purified as described in the above step 1, and ligated into pcDNA3.1 that was precut with HindIII, filled-in with Klenow enzyme, and then digested with EcoRI. Identity of the DIP-encoding plasmid was verified by restriction with PauI, an enzyme having a unique restriction site present only in the DIP1 coding sequence. This vector was used for the transfection studies. All standard molecular biology procedures were carried out as described in Sambrook et al. (Sambrook, Fritch, Maniatis, Molecular cloning; A laboratory manual, Cold Spring Harbour Laboratory Press, pp 16.66, 1989).

Example 3

Methods for Evaluation of the Cell Survival-Promoting Effect of DIP1 a. Cell cultures:

1. HeLa cells: Human cervical carcinoma cells (HeLa) were grown in Dulbecco's modified Eagle's medium (DMEM), supplemented with 10% fetal calf serum (FCS) and 1% penicillin-streptomycin-Nystatin solution (Biological Industries, Israel), and 1% L-Glutamine solution (2 mM, biological Industries, Israel). Cells were grown in monolayer at 37° C. in 5% $CO_2$.

2. Kidney 293 cells (T): Human embryonic kidney 293 cells were grown in the conditions described for the HeLa cells.

b. Models of Apoptosis:

Three model systems of cell death were used:

1. Apoptosis induced by dopamine: Exposure of cells to dopamine at 100–500 micromolar for 24 hours induces cell death characteristic of apoptosis (Ziv I, et al., Neurosci Lett 170:136–140, 1994; Offen D, et al., Biochim Biophys Acta 1268:171–177, 1995; Masserano J M, et al., Mol Pharmacol 50:1309–1315, 1996; Shirvan A, et al., J. Neurochem 69:539–549, 1997; Corona V., et al., J. Neurochem 69:1870–1881, 1997; Velez-Pardo C, et al., Pharmacol Toxicol 80:76–84, 1997; Shinkai T, et al., J Neurosci Res. 393–399, 1997; Simantov R, et al., Neuroscience 74:39–50, 1996; Gabby M, et al., Neuropharmacology 35:571–578, 1996). The apoptosis-triggering effect of dopamine has been observed in numerous cell types including Hela cells, and these effects have been shown to be blocked by forced ectopic over expression of Bcl-2 (Ziv I, et al., Apoptosis 2:149–155, 1997; Offen D, et al., Cell Mol Neurobiol 17:289–304, 1997).

2. Apoptosis induced by hydrogen peroxide: Exposure to hydrogen peroxide has been shown to induce apoptotic cell death in various cell types (Hoyt K R et al., Neurochem Res 22:333–340, 1997; Li P F et al., 404: 249–252, 1997; Forrest V J et al., Free Rad Biol Med 16:675–684, 1994).

3. Apoptosis induced by Bax. This model utilizes an in vitro assay system for regulation of cell death by the Bcl-2 family of proteins: Cells were grown as described above in example 3a. Cells from log phase of growth were harvested using trypsin/EDTA and resuspended at a density of $5.0 \times 10^6$ cells/ml in 400 µl PBS. Cell suspension was then transferred to electroporation chambers containing a marker plasmid (pCDNA/Lac z) encoding beta-galactosidase as a reporter gene (10 µg)+a control plasmid (pCDNA), to bring total plasmid quantity to 23 micrograms+one of the following regimens:

1. An expression plasmid, encoding Bcl-2 (0.42 µg)
2. An expression plasmid, encoding Bax (0.42 µg).
3. Bcl-2-encoding plasmid+Bax-encoding plasmid (0.42 µg each).
4. Test compound, or an expression plasmid encoding for the test peptide+either Bcl-2-encoding plasmid or Bax-encoding plasmid or both.
5. Control: only the marker plasmid.

After one minute of incubation, electroporation was performed at 1050 µF and 220 V for a duration of 10–30 ms, using an Equibio gene pulser. Cells from the cuvettes were then pooled into a complete medium with 10% FCS, and $1 \times 10^6$ cells were aliquoted into 3.5 cm plates. At 18 hours post-transfection, cell viability was assessed through measurement of beta-galactosidase activity by standard methods (Sambrook, Fritch, Maniatis, Molecular cloning; A laboratory manual, Cold Spring Harbour Laboratory Press, pp 16.66, 1989). OD values were expressed as percent of control, and statistical significance was evaluated by appropriate parametric or non-parametric statistical tests.

Figure 4:
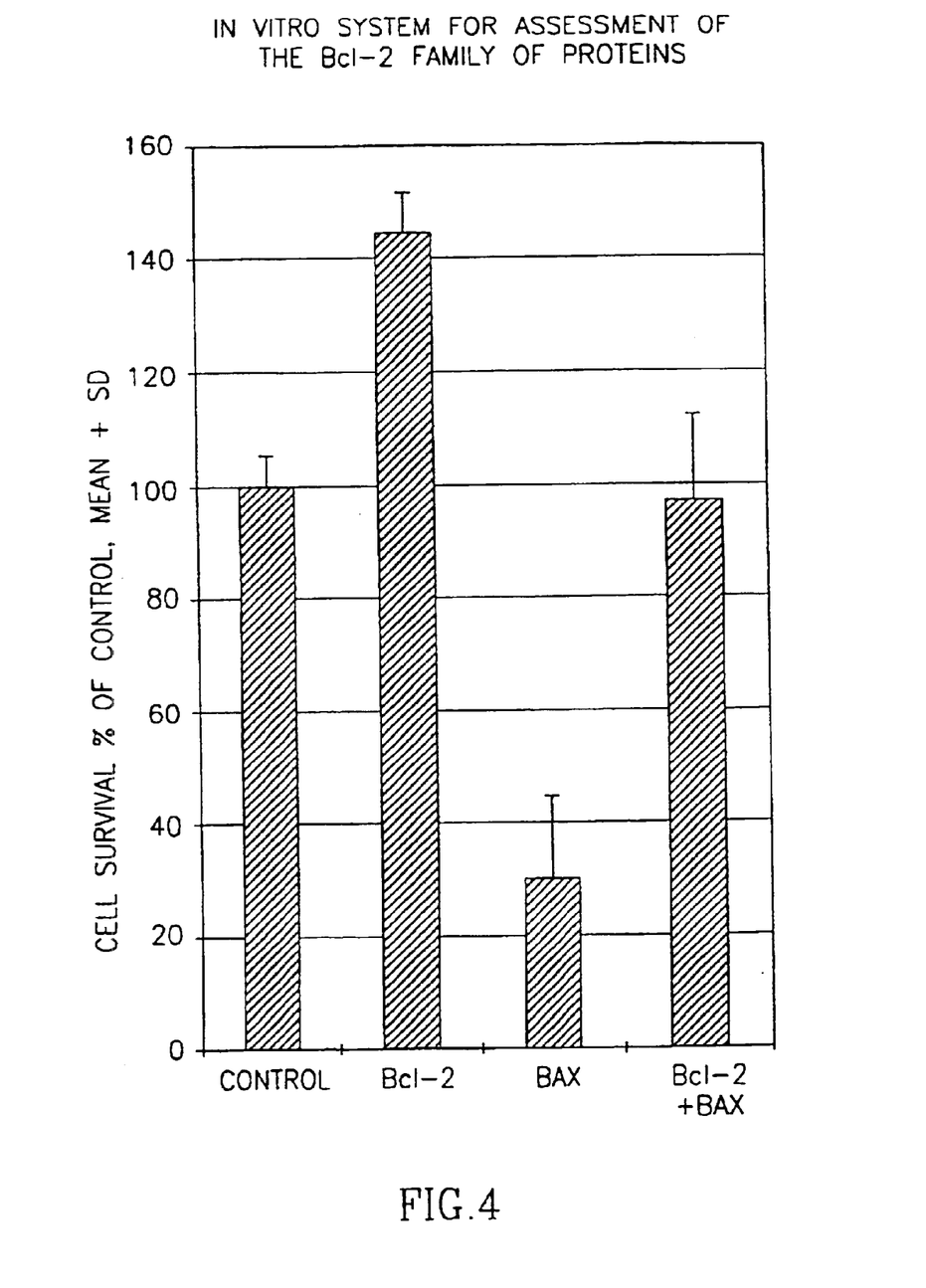
FIG. 4: In vitro assay system for the Bcl-2 family of proteins

As shown in FIG. 4, induced-expression of Bcl-2 in this system increases cell viability. Conceivably, it reflects the activity of Bcl-2 in inhibition of naturally-occurring cell death in culture and/or inhibition of cell death induced by the electroporation procedure. By contrast, as also shown in FIG. 4, Bax manifests a marked death-inducing effect, and this cell-killing effect of Bax can be markedly counteracted by co-transfection with Bcl-2. This in vitro assay system therefore reproduces effectively the expected activity of these major members of the Bcl-2 family (Oltvai Z N et al., Cell 74:609–619, 1993; Han J et al., Genes Dev 10:461–477, 1996; Zha H et al., Mol Cell Biol 16:6494–6508, 1996).

Example 4

DIP1 Inhibits Dopamine-Induced Cell Death

The objective of the experiment was to evaluate the ability of DIP1 to inhibit cell death induced by dopamine in HeLa cells.

Methods: DIP1 was synthesized as described above in Example 1, and introduced into the cells with the reporter plasmid pCDNA/Lac-z, by the electroporation procedure as described above in Example 3.b.2. Five hours after electroporation, cells were exposed to dopamine (150 µM and 300 µM, Sigma, Ltd., Israel) for 18 hours. Cell viability was then evaluated by the measurement of the beta-galactosidase activity, as specified above.

Results: As described in FIG. 5, dopamine induced a dose-dependent cell death, reflected by reduction of cell survival to 30.8+6.0 and 8.4+7.0 percent of control, following exposure to 150 and 300 µM of dopamine, respectively, for 18 hours. DIP1 manifested a marked protective effect against dopamine toxicity, raising cell survival rates to 75.4+9.0% and 40.2+8.0% respectively ($P<0.001$).

Conclusion: DIP1 is a potent inhibitor of dopamine-induced cell death, as evaluated in this experimental system.

Example 5

DIP1 Increases Cell Survival Rate and Inhibits Bax-Induced Cell Death, thus Mimicking the Effect of Bcl-2.

The objective of this experiment was to test the effect of DIP1 on cell survival, in the in vitro assay for regulation of cell death by the Bcl-2 system.

Methods: An expression plasmid, encoding the DIP1 (synthesized as described above in Example 2) was used. The plasmid was then introduced into the assay system of the Bcl-2 proteins, as described above in Example 3.b.3.

Figure 6:
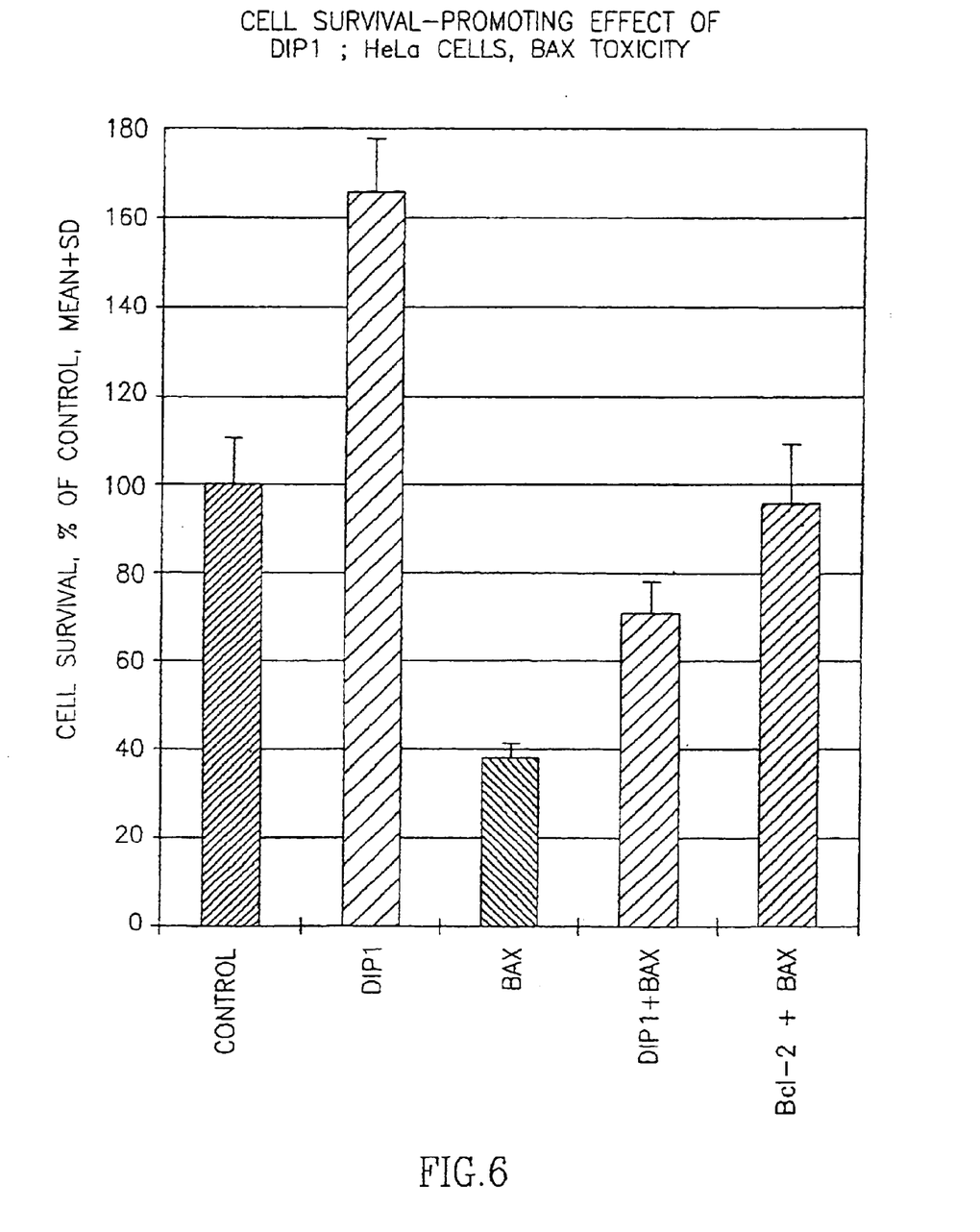
FIG. 6: RY peptide increases cell survival rate and inhibits Bax-induced cell death

Results: As shown in FIG. 6, cells transfected by electroporation with DIP1 manifested markedly enhanced cell viability as compared to controls, similar to the effect of Bcl-2 (FIG. 4). Moreover, DIP1 tranfection conferred marked protection against Bax death-inducing effect, reflected by a cell survival rate of 71.4+9.4% of control, versus 37.0+2.2% ($p<0.001$), similar to the effect of Bcl-2.

Conclusion: As evaluated in this experimental system, DIP1 increases cell survival following electroporation and inhibits the death-inducing effect of Bax. These effects may be therefore regarded as mimicking the effect of Bcl-2.

Example 6

DIP1 Inhibits Cell-Killing Effect of Bax on Embryonic Kidney 293T Cells

The objective of this experiment was to show the effect of DIP1 in counteracting the cell-killing effect of Bax, in a different model system (non-HeLa cells, non-electroporation-mediated transfection).

Methods: Human embryonic kidney 293T cells were grown as specified in Example 3.a. Cells were co-transfected using the Superfect Transfection Kit (Quiagen), with 5 µg total DNA of the following effectors: pCDNA/Lac-z reporter plasmid and one of the following:

1). Expression plasmid encoding DIP1.
2). Expression plasmid encoding Bax.
3). Expression plasmids, encoding Bax and DIP1.

After 18 hours, the cells were harvested for beta-galactosidase activity assay.

Figure 7:
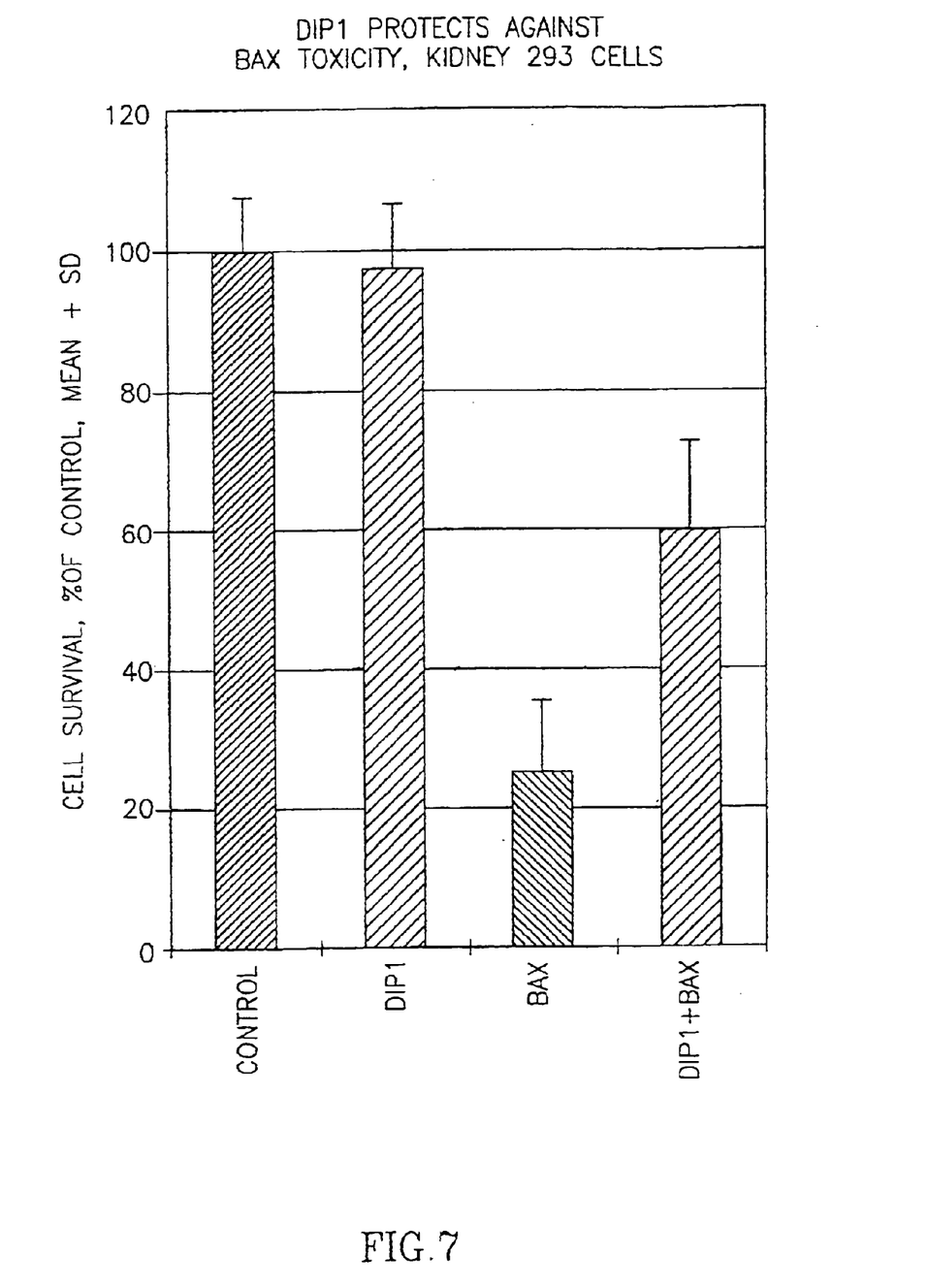
FIG. 7: RY peptide inhibits cell-killing effect of the Bax on embryonic kidney 293T cells

Results: As shown in FIG. 7, the DIP1 was markedly active in counteracting Bax toxicity.

Conclusion: DIP1 is a potent inhibitor of Bax cell-killing effect in this experimental system.

Example 7

DIP1 Inhibits Hydrogen Peroxide Toxicity in Hela Cells

The objective of this experiment was to examine the ability of DIP1 to inhibit cell death induced by hydrogen peroxide in HeLa cells.

Methods: Two methods for administration of DIP1 were employed:

1) Hela cells were co-transfected (via electroporation), with two expression vectors: (1) Expression vector encoding for the reporter gene beta-galactosidase. (2). Expression vector encoding for DIP1 (as described in Example 2)-

2) Hela cells were co-transfected (via electroporation), with the expression vector encoding for beta-galactosidase and with the synthetic DIP1 (as described in Example 1).

Five hours after the electroporation procedure, cells were tested with 100 μM and 200 μM of hydrogen peroxide (Merck, Inc. USA), for 18 hours.

Figure 8A:
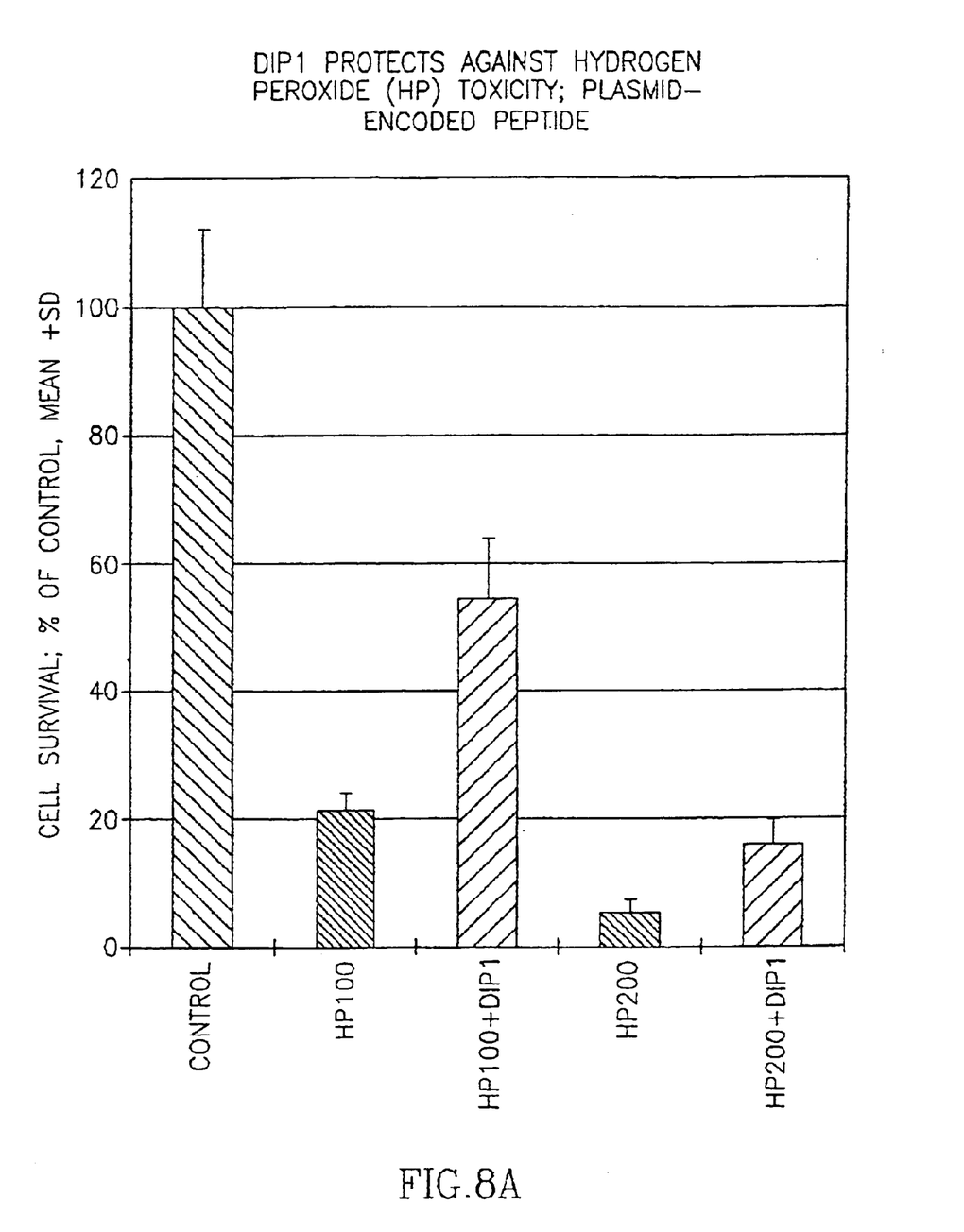
FIG. 8A: Plasmid encoded RY peptide protects against hydrogen peroxide toxicity
Figure 8B:
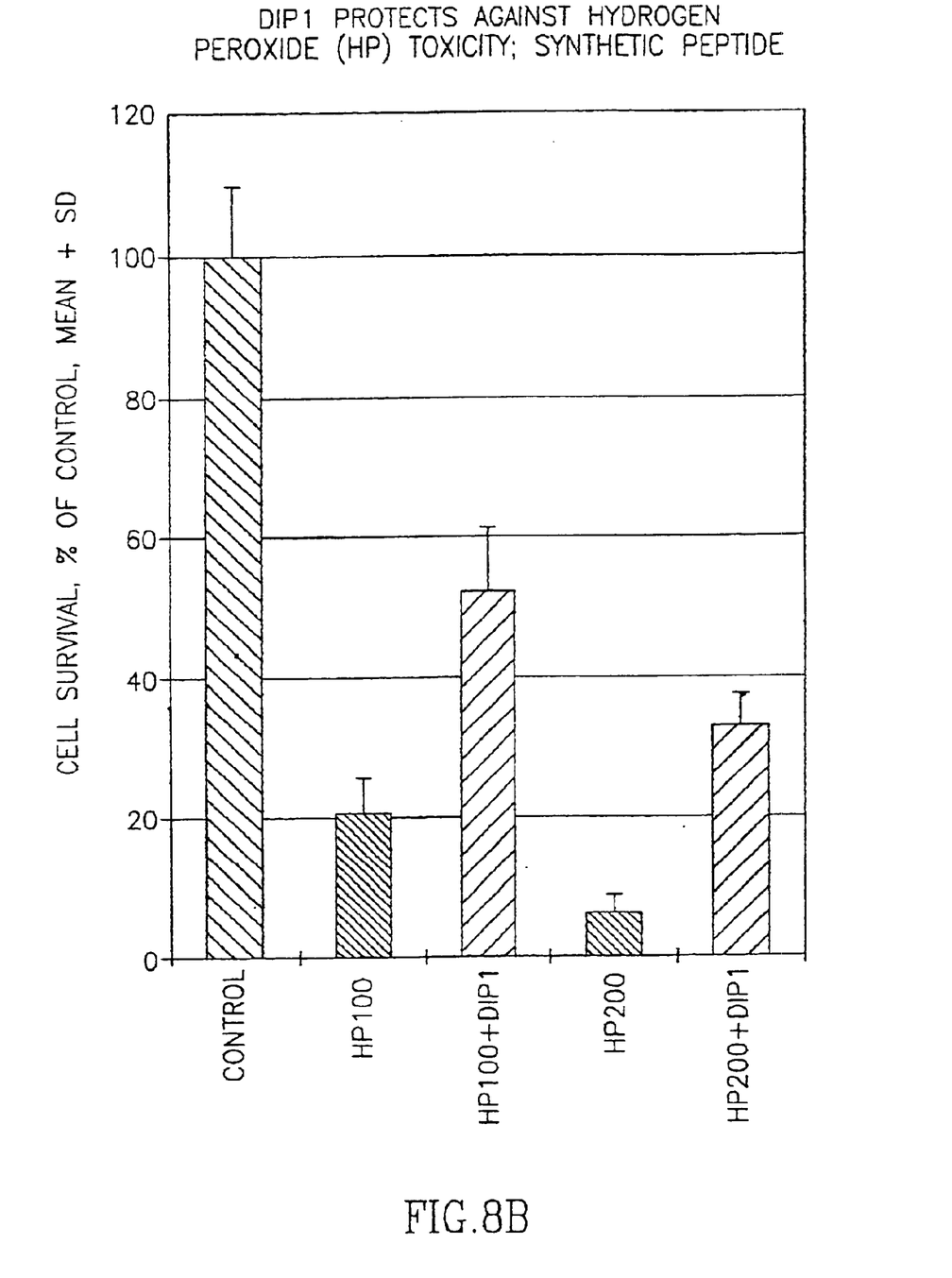
FIG. 8B: Synthetic RY peptide protects against hydrogen peroxide toxicity.

As described in FIGS. 8A and 8B, hydrogen peroxide treatment reduced cell survival rate to 20.4±2.8 and 5.8±2.1 percent of control (mean±SD), respectively. DIP1, both plasmid-encoded and synthetic peptide, manifested a marked protective effect. Cell survival rate in the presence of hydrogen peroxide and plasmid-encoded DIP1 was increased to 53.9±9.3 and 15.3±4.2 percent of control, respectively. Protective effect of synthetic DIP1 was reflected by increase of cell survival rate to 53.3±8.8 and 33.4±3.7%, respectively (p<0.001).

Figure Legends:

FIG. 1: Structure of the DIP Region

NMR solution three-dimensional structure of Bcl-xL (Muchmore S W, et al., Nature 381: 335–341, 1996) was extracted from the Brookhaven Protein Data Bank, Accession No. 1LXL. The DIP region (Phe97-Ph105), is marked. As shown, this small region is located on the outer surface of the protein, forming an almost closed loop.

FIG. 2: RP-HPCL of the Purified DIP1.

RP-HPLC (Reversed phase high performance liquid chromatography) of purified DIP1 (H-Phe-Glu-Leu-Arg-Tyr-Arg-Arg-Ala-Phe-OH. The peptide was analysed on $C_{18}$-5 μm Phenomenex Kromasil column (4.6 mm. I.D.×25 cm). A sample was eluted using the following gradient: A, distilled $H_2O$ 0.05% TFA (Trifluoroacetic acid)/; Acetonitrile 0.05% TFA; λ=214; flow 1 ml/min. t=0% B=5 t=30 min % B=50. The numbers on the y axis indicate mili absorbance units. The numbers on the X axis indicate minutes. The numbers on the peaks of the graph indicate the retention time.

FIG. 3: MS-(FAB) of the Purified DIP1

MS-(FAB) (Mass spectra-Fast atomic bombardment) of purified DIP1 H-Phe-Glu-Leu-Arg-Tyr-Arg-Arg-Ala-Phe-OH. The numbers on the y axis indicate the relative ion abundance of the ms detector. On the x axis the mass per charge M/z is calculated for $C_{59}H_{89}N_{18}O_{13}$ ($MH^+$) 1257.7, and the M/z found was 1258.4.

FIG. 4: In Vitro Assay System for the Bcl-2 Family of Proteins

HeLa cells were co-transfected with a beta-galactosidase reporter plasmid in combination with either a control plasmid (vector), a plasmid expressing Bcl-2 or Bax, or both plasmids expressing Bcl-2 and Bax, using electroporation procedure. Cell viability was assessed at 18 hours past the electroperotion, by measurement of beta-galactosidase activity.

Figure 5:
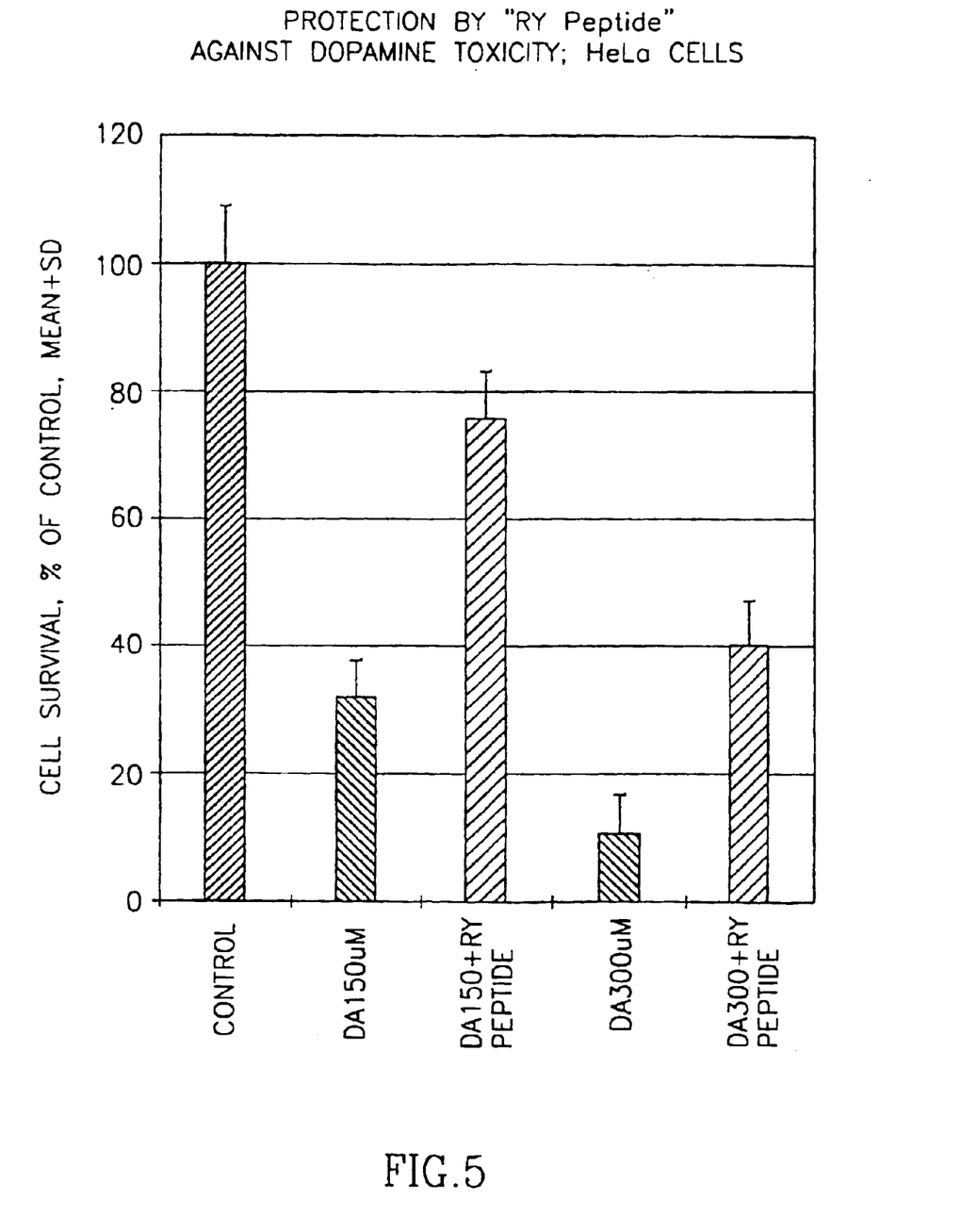
FIG. 5: RY peptide protects HeLa cells against dopamine toxicity

FIG. 5: DIP1 Protects HeLa Cells Against Dopamine Toxicity:

Synthetic DIP1 was introduced into HeLa cells with a beta-galactosidase reporter plasmid by electroporation. After five hours, cells were exposed to dopamine (150 μu and 300 μM, Sigma, Ltd., Israel) for 18 hours. Cell viability was then evaluated by measurement of the beta-galactosidase activity.

FIG. 6: DIP1 Increases Cell Survival Rate and Inhibits Bax-Induced Cell Death, thus Mimicking the Effect of Bcl-2.

HeLa cells were co-transfected by electroporation with an expression plasmid encoding the DIP1 and a beta-galactosidase reporter plasmid, and introduced into the assessment system of the Bcl-2 proteins, as described above in Example 3.b.3 and FIG. 4. Cell viability was evaluated 18 hours after the electroporation by measurement of beta-galactosidase activity.

FIG. 7: DIP1 Inhibits Cell-Killing Effect of Bax on Embryonic Kidney 293T Cells

Human embryonic kidney 293T cells were co-transfected by electroporation with a reporter plasmid encoding beta-galactosidase, in combination with either an expression plasmid encoding DIP1; an expression plasmid encoding Bax; or expression plasmids encoding Bax and DIP1. Cell viability was evaluated after 18 hours, by measurement of beta-galactosidase activity.

FIG. 8A: Plasmid-encoded DIP1 Protects Against Hydrogen Peroxide Toxicity.

HeLa cells were co-transfected via electroporation with an expression plasmid encoding for DIP1, together with a reporter plasmid encoding for beta-galactosidase. Five hours after electroporation, cells were treated with either 100 μM or 200 μM of hydrogen peroxide (HP) for 18 hours. Cell viability was then evaluated by determining beta-galactosidase activity.

FIG. 8B: Synthetic DIP1 Protects Against Hydrogen Peroxide Toxicity.

HeLa cells were co-transfected via electroporation with DIP1 synthetic peptide, together with a reporter plasmid encoding for beta-galactosidase. Five hours after electroporation, cells were treated with either 100 μM or 200 μM of hydrogen peroxide (HP) for 18 hours. Cell viability was then evaluated by determining beta-galactosidase activity.

What is claimed is:

1. An isolated and purified peptide of the RY domain having an amino acid sequence of general formula I comprising a sequence of the following amino acids:

$$X_1-X_2-X_3-X_4-X_1-X_4-X_4-X_3-X_1 \quad \text{I}$$

$X_1$=Phe, Tyr, or any amino acid having a substituted aromatic residue;

$X_2$=Glu, Asp, Ser, or any amino acid having a —$(CH_2)_n$— COO residue, wherein n=0–3;

$X_3$=Asp, Thr, any aliphatic amino acid or any of amino acids $X_4$; and $X_4$=Arg, Lys, or any amino acid having a —$(CH_2)_n$—$NH_3^+$ residue, or a —$(CH_2)_n$—NH—C($NH_3^+$)$NH_2$ residue wherein n=0–4.

2. A peptide according to claim 1, wherein Methionine (Met) is connected to the N-terminal of the sequence of general formula L.

3. A peptide according to claim 1 or 2 wherein in the sequence of general formula I, the sequence is $X_4$—$X_1$—$X_4$—$X_4$ stands for Arg-Tyr-Arg-Arg.

4. A peptide according to claim 3, wherein the sequence is preceded by $X_3$=Arg.

5. A peptide according to claim 1, wherein the substituted aromatic residue of $X_1$ is Phenyl —$(CH_2)_n$—.

6. A peptide according to claim 1, wherein the aliphatic amino acid of $X_3$ is selected among Leu, Ile, Ala, Gly and Val.

7. Phe-Glu-Leu-Arg-Tyr-Arg-Arg-Ala-Phe.

8. Phe-Ser-Arg-Arg-Tyr-Arg-Arg-Asp-Phe.

9. Phe-Glu-Thr-Arg-Phe-Arg-Mg-Thr-Phe.

10. A pharmaceutical composition comprising as active ingredient a RY peptide according claim 1.

11. A pharmaceutically composition according to claim 10, comprising a pharmaceutically acceptable carrier.

12. A method for the treatment of disorders of inappropriate activation of apoptosis comprising the step of administering a pharmaceutical composition according to claim 10 to a subject in need thereof.

13. A method for increasing the number of viable cells in a biological tissue comprising the step of administering a pharmaceutical composition according to claim 10 to a subject in need thereof.

14. A method for the enhancement for the survival of biological cells comprising the step of administering a pharmaceutical composition according claim 10 to a subject in need thereof.

* * * * *

SEQUENCE LISTING

<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Phe Glu Leu Arg Tyr Arg Arg Ala Phe
 1               5

```
<210> SEQ ID NO 2
<211> LENGTH: 9
<212> TYPE: PRT
<213> ORGANISM: Homo sapiens

<400> SEQUENCE: 2

Phe Ser Arg Arg Tyr Arg Arg Asp Phe
  1               5

<210> SEQ ID NO 3
<211> LENGTH: 9
<212> TYPE: PRT
<213> ORGANISM: Homo sapiens

<400> SEQUENCE: 3

Phe Glu Thr Arg Phe Arg Arg Thr Phe
  1               5

<210> SEQ ID NO 4
<211> LENGTH: 7
<212> TYPE: PRT
<213> ORGANISM: Homo sapiens

<400> SEQUENCE: 4

Leu Asp Ser Asn Met Glu Leu
  1               5

<210> SEQ ID NO 5
<211> LENGTH: 9
<212> TYPE: PRT
<213> ORGANISM: Homo sapiens

<400> SEQUENCE: 5

Ile Asn Arg Arg Tyr Asp Ser Glu Phe
   1               5

<210> SEQ ID NO 6
<211> LENGTH: 4
<212> TYPE: PRT
<213> ORGANISM: Homo sapiens

<400> SEQUENCE: 6

Arg Tyr Arg Arg
  1

<210> SEQ ID NO 7
<211> LENGTH: 73
<212> TYPE: DNA
<213> ORGANISM: Homo sapiens

<400> SEQUENCE: 7
cgacggaatt cagtggatcc atgtttgaac tgcggtaccg gcgcgcgttc tagactagta      60
acggccgcca gtg                                                         73

<210> SEQ ID NO 8
<211> LENGTH: 34
<212> TYPE: DNA
<213> ORGANISM: Homo sapiens

<400> SEQUENCE: 8
gcgtctagat gctcgacctg cagttggacc tggg                                  34
```